United States Patent [19]
Ottmann et al.

[11] 3,979,427
[45] Sept. 7, 1976

[54] CONVERSION OF NITROSO COMPOUNDS TO ISOCYANATES

[75] Inventors: Gerhard F. Ottmann, Wuppertal-Elberfeld, Germany; David F. Gavin, Cheshire; Ehernfried H. Kober, Hamden, both of Conn.

[73] Assignee: Olin Corporation, New Haven, Conn.

[22] Filed: Jan. 21, 1969

[21] Appl. No.: 792,833

[52] U.S. Cl. .................................. 260/453 PC
[51] Int. Cl.² ................................. C07C 118/06
[58] Field of Search .......................... 260/453 PC

[56] References Cited
UNITED STATES PATENTS
3,467,687  9/1969  Hardy et al. ............... 260/453

*Primary Examiner*—Elbert L. Roberts
*Assistant Examiner*—Dolph H. Torrence
*Attorney, Agent, or Firm*—Donald F. Clements; Thomas P. O'Day

[57] ABSTRACT

A process for preparing an organic isocyanate by reacting an organic nitroso compound with carbon monoxide in the presence of a catalyst comprised of a mixture of a noble metal and a Lewis acid.

1 Claim, No Drawings

CONVERSION OF NITROSO COMPOUNDS TO ISOCYANATES

This invention relates to a new method of preparing organic isocyanates. More particularly, it relates to the preparation of isocyanates by reacting an organic nitroso compound and carbon monoxide under elevated temperature and pressure conditions and in the presence of a suitable catalyst.

Tons of isocyanates, particularly aromatic isocyanates, are produced and consumed annually. Commercial needs are currently satisfied by a process which comprises reacting phosgene with an amino compound corresponding to the desired isocyanate, the reaction being conducted at elevated temperatures and pressures. Both phosgene and aromatic amino compounds are relatively expensive materials, and operations are often complicated because of the extreme toxicity of phosgene gas. For these and other reasons, there is a definite need for a new method to serve as a commercial route to isocyanates.

It is an object of this invention to provide a method by which isocyanates can be prepared from different starting materials. It is a further object to provide a method by which isocyanates can be prepared without use of phosgene. Other objects will become apparent from the ensuing description of this invention.

In accordance with this invention, it has been discovered that these objects can be efficiently accomplished by a new process which requires as its essential starting materials an organic nitroso compound, carbon monoxide and a special type of catalyst. The reaction of this invention effects the replacement of the oxygen on the nitroso radical by carbonyl with the consequent formation of an isocyanate. The reaction can be schematically represented as follows:

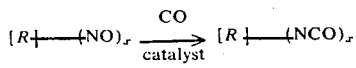

In the foregoing equation, the symbol "R" is intended to represent an organic radical and "x" represents an integer. The foregoing reaction may be conducted under substantially anhydrous conditions in a substantially hydrogen-free atmosphere.

The reaction between the nitroso compound and carbon monoxide may be carried out in an autoclave or any other high pressure reactor. A simple procedure is to charge the nitroso compound and catalyst in a solvent, if one is employed, into the reaction vessel, introduce the proper amount of carbon monoxide, and then heat the mixture to obtain the desired reaction pressure and temperature. The reaction can be conducted as a continuous operation or batchwise. Of course, the order of addition of the reactants may be varied to suit the particular apparatus which is employed. For example, the reactants may be introduced on a continuous basis into the heated reactor while, at the same time, the product is withdrawn. The reaction product is recovered and then treated by conventional procedures to effect separation of isocyanate from unreacted starting material, solvent, by-product, etc.

The present invention provides a generally applicable process for converting either mono- or poly-nitroso derivatives to the corresponding isocyanates.

Typical of the nitroso compounds which can be converted to isocyanates are carbocyclic aromatic derivatives such as nitrosobenzene, o-, m- and p-dinitrosobenzene, 1-nitrosonaphthalene and 1,2-dinitrosonaphthalene. Likewise, heterocyclic derivatives may also be used.

The process of this invention is applicable to nitroso compounds with or without other substituents, such as alkyl, alkenyl, alkoxy, halogen, acylamido, hydroxy, nitro, mercapto, alkylthio, carboxy, carbalkoxy, cyano, acyl, sulfo, sulfonyl, sulfamyl, carbamyl, phosphono, phosphino and silyl radicals.

Among the substituted nitroso compounds useful as starting materials herein, are p-nitrosotoluene, p-nitrosoanisole, p-nitrosophenol, p-nitroso-m-cresol, 2-ethylnitrosobenzene, 4-chloronitrosobenzene, 4-bromonitrosobenzene, 4-fluoronitrosobenzene, p-nitroso-N,N-dimethylaniline, p-nitrosobenzoic acid, 1-nitroso-2-naphthol, 2-nitroso-p-xylene, 2-fluoro-4-nitrosotoluene, 1-methoxy-4-nitrosonaphthalene, 3,4-dinitrosotoluene, 4-methylthio-1-nitrosobenzene and 4-nitro-1-nitrosobenzene. Substituents do not, in general, interfere with the reaction of this invention. Certain substituents may themselves react with carbon monoxide concurrent with the desired reaction, but the latter reaction, nevertheless, occurs. Other groups in the nitroso starting material may react with the isocyanate group, thus yielding derivatives of isocyanates as reaction products. Still others may sterically retard the rate of isocyanate formation without preventing it entirely. With these qualifications, the process of this invention is applicable to any organic compound with a nitroso group.

Reaction conditions can be varied over a wide range provided several requirements with respect to pressure and temperature are met. Pressures within the reactor must be in the range of about 40 p.s.i. to 100,000 p.s.i. or higher. Preferably, the pressure should be above 1,000 p.s.i. The reaction will proceed at temperatures above 60°C., and preferably between 150°C., and the temperature of decomposition of either the starting material or the product. The temperature will vary inversely with residence time of material in the reactor. With more highly reactive starting materials, less stringent conditions may be employed. The particular conditions for a given reactant are easily determined in accordance with the foregoing principles.

It is desirable that a solvent be employed when the nitroso compounds are solids under the reaction conditions. Suitable solvents are anhydrous liquids in which the nitroso compound is soluble or dispersible, e.g., benzene, toluene, xylene, aliphatic halogenated hydrocarbons such as 1,1,2-trichloro-1,2,2-trifluoroethane and halogenated aromatic hydrocarbons such as monochlorobenzene, dichlorobenzene and trichlorobenzene. In one embodiment, the solvent, as well as the other materials charged into the reactor, are anhydrous, since in the presence of water, isocyanates are converted to urea derivatives.

The amount of carbon monoxide pumped into the reactor should be sufficient to provide at least 2 moles of carbon monoxide per nitroso group. Preferably, however, a large excess should be employed to give the super-atmospheric pressures required for preferred operation of the present invention.

The catalyst for the reaction of this invention comprises a noble metal and a Lewis acid as defined in the reference book by Jack Hine, PHYSICAL ORGANIC CHEMISTRY, 1962, McGraw-Hill Book Company, New York. According to the reference, Bronsted acids are included by the term "Lewis acids". The noble metal may be used either in a metallic or a chemically combined state. It may be deployed either with or without a physical support. Among the noble metals which can be employed are platinum, palladium, ruthenium, rhodium, osmium, and iridium. Among the chemical forms of these metals which can be used herein are oxides, sulfates, nitrates, halides, carbonates, sulfides, oxalates, and the like. Typical useful compounds of noble metals include platinum oxide, platinum dioxide, platinum dibromide, platinum dichloride, platinum tetrachloride, platinous cyanide, and platinum sulfate; palladium halides such as palladium dibromide, palladium dichloride, palladium difluoride and palladium diiodide; rhodium halides such as rhodium tribromide, rhodium trichloride, rhodium trifluoride, and rhodium triiodide; palladium oxides such as palladium suboxide ($Pd_2O$), palladium monoxide (PdO), and palladium dioxide ($PdO_2$); rhodium oxides such as rhodium monoxide (RhO), rhodium sesquioxide ($Rh_2O_3$), and rhodium dioxide ($RhO_2$); ruthemium trichloride ($RuCl_3$), ruthenium pentafluoride ($RuF_5$), ruthenium hydroxide [$Ru(OH_2)$], ruthenium dioxide ($RuO_2$), and ruthenium tetraoxide ($RuO_4$); mixtures thereof, and the like.

The Lewis acid component of the catalyst can be a halide (e.g., an iodide, bromide, chloride or fluoride), an acetate, a sulfate or a phosphate of a metal such as tin, titanium, gallium, iron, aluminum, cobalt or copper.

As specific examples of Lewis acids one can name ferric chloride, ferrous chloride, stannic chloride, stannous chloride, aluminum chloride, titanium tetrachloride, aluminum bromide, gallium trichloride, cobalt iodide, cobalt chloride and cupric chloride. Additional examples of the salt type of Lewis acids are listed in the reference book by George A. Olah, FRIEDEL-CRAFTS AND RELATED REACTIONS, Volume I, 1963, Int. Publ., New York.

An example of the Bronsted acid type of Lewis acid is anhydrous hydrogen chloride. Other Bronsted acids may be used providing they do not irreversibly react with the isocyanate product. Examples of such reactions are to be found in "Recent Advances in Isocyanate Chemistry" by R. G. Arnold et al., Chemical Reviews 57, 47 (1957).

Within the group of useful Lewis acids, it is preferred to use strong Lewis acids having a halide anion. Chlorides and iodides of iron, cobalt and aluminum are especially preferred.

The physical form of the catalyst can be varied to suit particular needs. The metals can be self-supported or deposited upon a support which disperses the metals so as to increase active surface area. Such porous supports include alumina, silica, carbon, barium sulfate, calcium carbonate, asbestos, bentonite, diatomaceous earth, Fuller's earth, and the like.

It is possible to deposit the noble metal on a support and form the Lewis acid component in situ by conducting the reaction in a vessel which can supply a cation, when using a solvent medium which can supply an anion under reaction conditions. Similarly a noble metal and a base metal capable of forming a Lewis acid (e.g., iron or aluminum) may be deposited on a porous support. This base metal, in conjunction with a solvent medium comprising a halogenated solvent (e.g., 1,1,2-trichloro-1,2,2-trifluoroethane or a similar halogenated aliphatic hydrocarbon), froms a Lewis acid under reaction conditions. Other means of forming the Lewis acid in situ will be apparent from these procedures.

A very useful catalytic system consists of 5 percent palladium, supported on alumina, and ferric chloride. The catalyst should be used in an effective amount. This amount will be determined by reaction pressure and temperature, purity of the nitroso starting material, etc. Once it is known that the desired reaction proceeds in the presence of a noble metal and Lewis acid catalyst, it is within ordinary means to determine how much of each will be used. It has been found that a useful range is in the area of about $10^{-1}$ to $10^{-5}$ mole of noble metal and $5 \times 10^{-2}$ to $5 \times 10^{-4}$ mole of Lewis acid per mole of nitroso group. Actually, as long as even trace amounts of the metals are present, reaction will proceed. The upper limit of catalyst usage is governed primarily by cost considerations. A preferred catalyst system will have about 0.2-0.001 mole of Lewis acid and 0.05 to 0.005 mole of noble metal per mole of nitroso group. Within these areas, the centers of the respective ranges are especially preferred, but this preferred range depends greatly on the equipment and conditions used, i.e., the amount of agitation, concentrations, temperature, pressure, etc.

This invention is illustrated in the following Examples, in which percentages are on a weight basis.

EXAMPLE 1

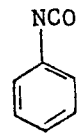

A suitable pressure vessel with stainless steel walls is charged with 90 parts of 1,1,2-trichloro-1,2,2-trifluoroethane, 10.7 parts (0.1 mole) of nitrosobenzene and 5 parts of 5 percent palladium on alumina. The pressure vessel is sealed and flushed 3 times with carbon monoxide. Carbon monoxide is introduced into the clave until a pressure of 2,800 p.s.i. is obtained. With agitation, the pressure vessel is heated to 170°C. The internal pressure is then about 4,000 p.s.i. After maintaining the temperature at 170°C. for 5 hours, the pressure vessel is cooled to room temperature, vented, flushed with nitrogen and opened. The solvent-soluble material is removed, and the pressure vessel is rinsed with additional solvent. The combined solvents are filtered, and the solvent is removed from the product by distillation under reduced pressure. The crude product is then distilled to give phenyl isocyanate.

EXAMPLE 2

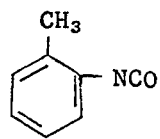

The general procedure of Example 1 is repeated, substituting an equivalent amount of o-nitrosotoluene for the nitrosobenzene, and using a temperature of 180°C. and pressure of 11,000 p.s.i. The product is o-tolyl isocyanate.

EXAMPLE 3

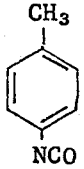

The general procedure of Example 1 is repeated, substituting an equivalent amount of p-nitrosotoluene for the nitrosobenzene and a pressure of 13,800 p.s.i. The product is p-tolyl isocyanate.

EXAMPLE 4

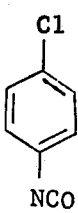

The procedure of Example 1 is repeated, substituting an equivalent amount of p-nitrosoanisole for the nitrosobenzene. The product is p-methoxyphenyl isocyanate.

EXAMPLE 5

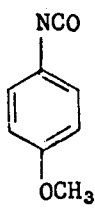

The procedure of Example 1 is repeated, substituting an equivalent amount of p-nitrosoanisole for the nitrosobenzene. The product is p-methoxyphenyl isocyanate.

EXAMPLE 6

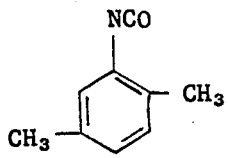

The procedure of Example 1 is repeated, substituting an equivalent amount of 2-nitroso-p-xylene for the nitrosobenzene. The product is 2,5-dimethylphenyl isocyanate.

EXAMPLE 7

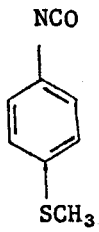

The procedure of Example 1 is repeated, substituting an equivalent amount of 4-methylthio-1-nitrosobenzene for the nitrosobenzene. The product is 4-methylthiophenylisocyanate.

EXAMPLE 8

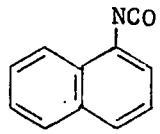

The procedure of Example 1 is repeated, substituting an equivalent amount of 1-nitrosonaphthalene for the nitrosobenzene. The product is 1-naphthyl isocyanate.

EXAMPLES 9–13

The general procedure of Example 1 is repeated, using different noble metal catalysts, temperatures and pressures shown below. Phenyl isocyanate is obtained.

| Example | Noble Metal Catalyst | Temperature (°C.) | Pressure (p.s.i.) |
|---|---|---|---|
| 9  | 5% Pd/BaSO$_4$   | 170 | 10,500 |
| 10 | 5% Pd/CaCO$_3$   | 180 | 13,500 |
| 11 | 5% Rh/alumina    | 180 | 11,500 |
| 12 | 5% Ru/alumina    | 170 | 11,500 |
| 13 | Pd Black         | 170 | 14,500 |

EXAMPLE 14

A tantalum lined autoclave is charged with 12.3 parts of nitrosobenzene, 0.73 part of anhydrous ferric chloride, 5 parts of 5% Pd/C and 100 parts of benzene. The clave is sealed, purged with nitrogen and pressurized with CO to 2,700 p.s.i. It is then heated with rocking at 190°C. for 5 hours, cooled, vented and discharged. The reaction mixture is filtered and the phenyl isocyanate is isolated as described in Example 1.

EXAMPLE 15

The procedure of Example 14 is repeated using 12.3 parts of nitrosobenzene, 80 parts of benzene, 10 parts of 5% palladium on carbon and 0.44 part of stannic chloride. After carbon monoxide is introduced to a pressure of 4,000 p.s.i., the pressure vessel is heated at 190°C. for 5 hours. Phenyl isocyanate is obtained.

EXAMPLE 16

The procedure of Example 14 is repeated using 12.3 parts of nitrosobenzene, 80 parts of benzene, 5 parts of rhodium on carbon and 1.41 parts of aluminum bromide. After carbon monoxide is introduced to a pressure of 3,000 p.s.i., the pressure vessel is heated at 190°C. for 5 hours. Phenyl isocyanate is obtained.

EXAMPLE 17

The procedure of Example 14 is repeated using 12.3 parts of nitrosobenzene, 80 parts of benzene, 5 parts of rhodium on carbon and 0.5 part of ferrous chloride. After carbon monoxide is introduced to a pressure of 2,700 p.s.i., the pressure vessel is heated at 190°C. for 5 hours. Phenyl isocyanate is obtained.

EXAMPLE 18

The procedure of Example 14 is repeated using 12.3 parts of nitrosobenzene, 80 parts of benzene, 5 parts of rhodium on carbon and 0.75 part of aluminum chloride. After carbon monoxide is introduced to a pressure of 3,000 p.s.i., the pressure vessel is heated at 190°C. for 5 hours. Phenyl isocyanate is obtained.

EXAMPLE 19

A 316 stainless steel autoclave having a volume of 300 ml. was secured to a rocking mechanism capable of rocking the autoclave and contents during the reaction. The autoclave was also provided with a heating means.

The autoclave was charged with 10.0 grams of nitroso benzene, 63 grams (73 ml.) of toluene, 0.5 grams of rhodium trichloride, and 0.5 grams of anhydrous cobalt iodide. The autoclave was closed and then charged with sufficient carbon monoxide to increase the pressure to 1400 psig. The autoclave was heated to a temperature of 200°C. for 2 hours. After cooling the autoclave was vented, the contents filtered and the filtrate was analyzed by vapor phase chromotography. The product contained 3.2 grams of phenyl isocyanate, which corresponded to a corrected yield of 29 percent phenyl isocyanate.

Various modifications of the invention, some of which have been disclosed above, may be employed without departing from the spirit of the invention.

What is claimed and desired to be secured by Letters Patent is:

1. In the process for preparing an aromatic isocyanate by reacting a carbocyclic aromatic nitroso compound with carbon monoxide at an elevated temperature and elevated pressure in the presence of a catalyst, the improvement which comprises employing as said catalyst a mixture of rhodium trichloride and cobalt iodide.

* * * * *